(12) United States Patent
Kawabata et al.

(10) Patent No.: US 8,670,404 B2
(45) Date of Patent: *Mar. 11, 2014

(54) INFORMATION DOWNLOADING APPARATUS AND MOBILE TERMINAL

(75) Inventors: Kazuo Kawabata, Kawasaki (JP); Yoshiharu Tajima, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 234 days.

This patent is subject to a terminal disclaimer.

(21) Appl. No.: 13/234,427

(22) Filed: Sep. 16, 2011

(65) Prior Publication Data

US 2012/0002585 A1 Jan. 5, 2012

Related U.S. Application Data

(63) Continuation of application No. PCT/JP02/09725, filed on Sep. 20, 2002, and a continuation-in-part of application No. 11/020,629, filed on Dec. 27, 2004, now Pat. No. 8,054,795.

(51) Int. Cl.
*H04W 4/00* (2009.01)

(52) U.S. Cl.
USPC ............ 370/330; 370/432; 370/436; 455/60; 455/62

(58) Field of Classification Search
USPC ............ 370/438, 395.4, 337, 347, 330, 432; 370/436; 455/60, 62
See application file for complete search history.

(56) References Cited

U.S. PATENT DOCUMENTS

| | | | |
|---|---|---|---|
| 4,155,040 A | 5/1979 | Harmon et al. | |
| 4,630,282 A | 12/1986 | Landers et al. | |
| 4,707,832 A | 11/1987 | Glenn et al. | |
| 5,659,545 A | 8/1997 | Sowles et al. | |
| 6,256,509 B1 | 7/2001 | Tanaka et al. | |
| 6,282,187 B1 | 8/2001 | Evans et al. | |
| 6,535,544 B1 | 3/2003 | Partyka | |
| 6,795,425 B1 | 9/2004 | Raith | |
| 6,804,528 B1 | 10/2004 | Laroia et al. | |

(Continued)

FOREIGN PATENT DOCUMENTS

EP 944275 9/1999
EP 1 143 630 10/2001

(Continued)

OTHER PUBLICATIONS

Office Action dated Jul. 21, 2008, issued in copending U.S. Appl. No. 11/020,629.

(Continued)

*Primary Examiner* — Ayaz Sheikh
*Assistant Examiner* — Mounir Moutaouakil
(74) *Attorney, Agent, or Firm* — Staas & Halsey LLP

(57) ABSTRACT

A technique for improving the efficiency of downloading transmission data is disclosed. An information downloading apparatus downloads differing sets of information to predetermined groups to which a mobile terminal may belong. This apparatus includes a channel selecting unit for selecting from plural information channels an information channel for transmitting transmission data and a transmitting unit for transmitting transmission data using the selected information channel. The channel selecting unit selects an information channel so that sets of transmission data with differing destination addresses may be transmitted through differing information channels. The transmitting unit transmits to each group, through a control channel, information pertaining to whether a set of transmission data exists, the information channel to be used if the set of transmission data exists, and the data length of the set of transmission data. The control channel includes time slots that are associated with the groups.

1 Claim, 16 Drawing Sheets

(56) References Cited

U.S. PATENT DOCUMENTS

| | | |
|---|---|---|
| 6,965,580 B1 | 11/2005 | Takagi et al. |
| 7,230,908 B2 | 6/2007 | Vanderaar et al. |
| 7,254,409 B2 | 8/2007 | Sato et al. |
| 7,257,127 B1 | 8/2007 | Cankaya |
| 7,639,739 B2 | 12/2009 | Rose et al. |
| 7,660,583 B2 | 2/2010 | Pekonen et al. |
| 2001/0053180 A1 | 12/2001 | Asia et al. |
| 2002/0105926 A1 | 8/2002 | Famolari et al. |
| 2002/0164986 A1 | 11/2002 | Briand et al. |
| 2002/0178455 A1 | 11/2002 | Poli et al. |
| 2002/0191567 A1 | 12/2002 | Famolari et al. |
| 2003/0099298 A1 | 5/2003 | Rose et al. |
| 2003/0115369 A1 | 6/2003 | Walter et al. |
| 2003/0157949 A1 | 8/2003 | Sarkkinen et al. |
| 2004/0156456 A1 | 8/2004 | Wu et al. |
| 2005/0131922 A1 | 6/2005 | Kennedy et al. |
| 2005/0186933 A1 | 8/2005 | Trans |
| 2005/0208942 A1 | 9/2005 | Pekonen et al. |
| 2007/0110149 A1 | 5/2007 | Langley et al. |
| 2008/0049743 A1 | 2/2008 | Zampetti |
| 2008/0208680 A1 | 8/2008 | Cho |
| 2008/0267126 A1 | 10/2008 | Vujcic et al. |
| 2009/0225691 A1 | 9/2009 | Son |
| 2009/0303918 A1 | 12/2009 | Ma et al. |
| 2010/0029274 A1 | 2/2010 | Deshpande et al. |
| 2010/0034076 A1 | 2/2010 | Kishiyama et al. |
| 2010/0080163 A1 | 4/2010 | Krishnamoorthi et al. |
| 2010/0135493 A1 | 6/2010 | Yoon et al. |
| 2010/0142431 A1 | 6/2010 | Kawabata et al. |
| 2011/0038285 A1 | 2/2011 | Kwon et al. |
| 2011/0074552 A1 | 3/2011 | Norair et al. |
| 2011/0158200 A1 | 6/2011 | Bachu et al. |

FOREIGN PATENT DOCUMENTS

| | | |
|---|---|---|
| JP | 5-130239 | 5/1993 |
| JP | 7-58689 | 3/1995 |
| JP | 7-283782 | 10/1995 |
| JP | 8-79167 | 3/1996 |
| JP | 8-322086 | 12/1996 |
| JP | 10-173785 | 6/1998 |
| JP | 11-69437 | 3/1999 |
| JP | 11-196447 | 7/1999 |
| JP | 11-266484 | 9/1999 |
| JP | 11-308674 | 11/1999 |
| JP | 11-331070 | 11/1999 |
| JP | 2000-44976 | 2/2000 |
| JP | 2000-101510 | 4/2000 |
| JP | 2000-115066 | 4/2000 |
| JP | 2000-138966 | 5/2000 |
| JP | 2000-224648 | 8/2000 |
| JP | 2001-168793 | 6/2001 |
| JP | 2001-197021 | 7/2001 |
| JP | 2001-285298 | 10/2001 |
| JP | 2001-308743 | 11/2001 |
| JP | 2001-308856 | 11/2001 |
| JP | 2002-158628 | 5/2002 |
| JP | 2002-185397 | 6/2002 |
| JP | 2002-186025 | 6/2002 |
| JP | 2002-204204 | 7/2002 |
| WO | 9506368 A1 | 3/1995 |
| WO | 9737456 A2 | 10/1997 |
| WO | WO 99/08461 | 2/1999 |

OTHER PUBLICATIONS

Office Action dated Jan. 25, 2008, issued in copending U.S. Appl. No. 11/020,629.
Office Action dated Sep. 29, 2009, issued in copending U.S. Appl. No. 11/020,629.
Office Action dated Oct. 1, 2010 in copending U.S. Appl. No. 11/020,629.
Office Action dated Mar. 17, 2010 in copending U.S. Appl. No. 11/020,629.
Office Action dated Mar. 15, 2011 in copending U.S. Appl. No. 12/702,617.
Notice of Allowance issued in copending U.S. Appl. No. 12/702,617 on Aug. 8, 2011.
Notice of Allowance issued in copending U.S. Appl. No. 11/020,629 on Jun. 16, 2011.
"Universal Mobile Telecommunications System (UMTS)", ETSI TR 125 925 V3.4.0, Mar. 2001, pp. 5-30.
Supplementary European Search Report, mailed Sep. 7, 2007 and issued in corresponding European Patent Application No. 02772884.9-2412.
Japanese Office Action mailed on Feb. 27, 2007 issued with respect to the corresponding Japanese Patent Application No. 2004-537526.
Japanese Office Action dated May 11, 2010 and issued in corresponding Japanese Application No. 2007-119558.
International Search Report dated Dec. 24, 2002 in corresponding International Application No. PCT/JP02/09725.
Japanese Patent Office Action, mailed Sep. 4, 2007 and issued in corresponding Japanese Patent Application No. 2004-537526.
Distributed multimedia system; from psu.edu VOK Li- Proceedings of the IEEE, 2002.
"Universal Mobile Telecommunications System (UMTS)", ETSI Standards, European Telecommunications Standards Institute, Sophia-Antipo, France, vol. 3-R2, No. V510, Jun. 2002.
"Skylight switch: New multicast WDM access switch architecture using photonic fast frequency hopping OCDMA technique" by Benhaddou, Driss, Ph.D., University of Missouri—Kansas City, 2002.
"A webcast virtual laboratory on a frequency modulation experiment" Ko, C.C.; Chen, B.M.; Chan, K.P.; Cheng, C.D.; Zeng, G.W.; Zhang, J.; Decision and Control, 2001.
Broadcast/multicast MPEG-2 video over broadband fixed wireless access networks; Hairuo Ma; El Zarki, M.; Network, IEEE vol. 12, Issue: 6 Digital Object Identifier: 10.1109/65.752647 Publication Year: 1998.
U.S. Appl. No. 11/020,629, filed Dec. 27, 2004, Kazuo Kawabata, et al., Fujitsu Limited.
U.S. Appl. No. 12/702,617, filed Feb. 9, 2010, Kazuo Kawabata, et al., Fujitsu Limited.

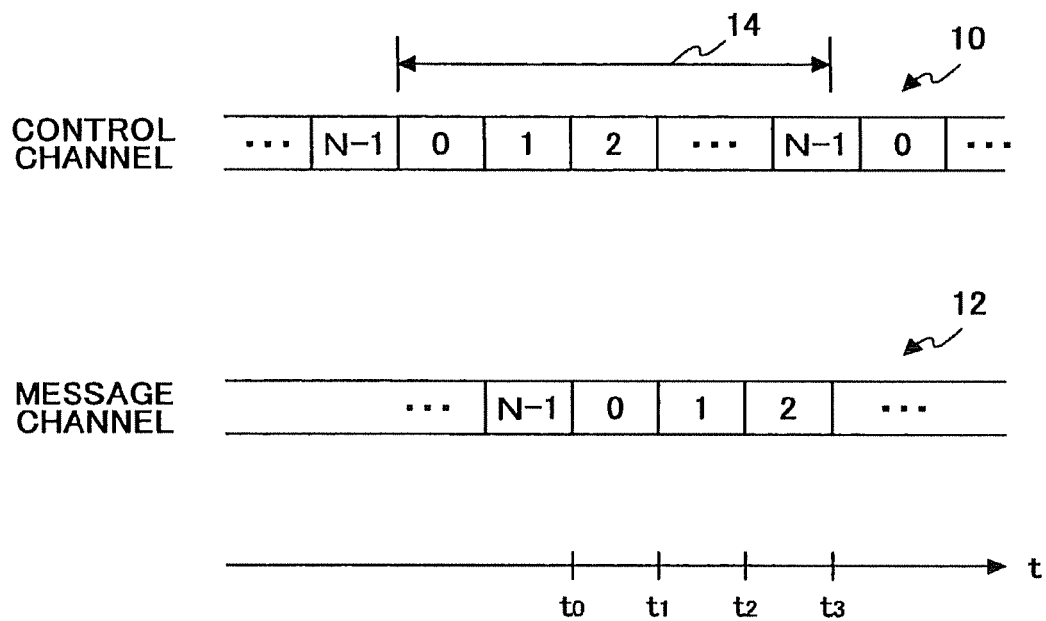

INFORMATION DOWNLOADING APPARATUS AND MOBILE TERMINAL

CROSS REFERENCE TO RELATED APPLICATIONS

This application corresponds to a U.S. continuation application filed under 35 USC 111(a) claiming benefit under 35 USC 120 and 365 (c) of PCT application JP2002/009725, filed on Sep. 20, 2002 and is related to and claims benefit of U.S. Ser. No. 11/020,629, filed Dec. 27, 2004, now U.S. Pat. No. 8,054,795, both of which are incorporated herein by reference in their entirety.

BACKGROUND OF THE INVENTION

1. Field of the Invention

The present invention relates generally to a technique for downloading identical information to plural mobile terminals, and particularly to an information downloading apparatus and a mobile terminal.

2. Description of the Related Art

In the above-described technical field, broadcasting technology for realizing simultaneous transmissive communication with respect to all mobile terminals, or multicast technology for realizing simultaneous transmissive communication with respect to mobile terminals that belong to a predetermined group may be used, for example.

FIG. 1 is a conceptual diagram illustrating an example of information downloading using multicast technology. In FIG. 1, a control channel 10 that is made up of time slots that are respectively assigned to various multicast groups, and a message channel 12 for actually downloading information in relation to the control channel 10 are shown. The control channel 10 is arranged into a repetition of super frames 14, and N time slots that are numbered from 0 to N−1, respectively, are included in each super frame 14. N (>0) may be set according to the number of different types of downloading information that are provided, and designates the number of groups to which a mobile terminal may belong.

FIG. 2 is a table illustrating the relation between a time slot number and a group (information content). For example, if information downloading pertaining to weather forecast is desired, a mobile terminal may be required to subscribe to the multicast group corresponding to slot number 1.

Referring back to FIG. 1, a mobile terminal may receive control channel information pertaining to the group to which it belongs. Such information may only be transmitted through a predetermined timeslot. Thereby, the mobile terminal may conserve its battery energy through intermittent reception to receive control data from the control channel only during the period corresponding to the time slot of the pertinent group to which the mobile terminal belongs. For example, if the mobile terminal belongs to the weather forecast group, it may receive signals from the control channel during the period of time slot 1, and may be configured to refrain from receiving signals during the periods of the other time slots. The control channel 10 includes information indicating whether download information exists, and the mobile terminal may be configured to extract this information. If it is determined that there is no transmission information, the mobile terminal may go back to a standby mode to receive the next control data from the control channel. On the other hand, if it is determined that transmission information exists, the mobile terminal may receive the transmission information that is transmitted through the message channel 12 after a predetermined time (offset time) elapses from the time slot 1 (i.e., after time t1). Similarly, mobile terminals belonging to other groups may also receive desired information using the control channel that indicates the existence of transmission information and the message channel 12 (e.g., if the desired information corresponds to baseball information, the information is transmitted after time t2; and if the desired information corresponds to stock information, the information is transmitted after time t3).

Japanese Laid-Open Patent Publication No. 2000-224648 relating to information downloading discloses a technique for creating a broadcast channel that is dedicated to broadcasting using a predetermined time slot from time slots provided for a control channel and a communication (message) channel, and transmitting broadcast data via this broadcast channel to thereby simultaneously transmit the broadcast data to plural mobile terminals.

However, in such prior art example, the time slots used for the information downloading implements a fixed signal format that is set beforehand. Thereby, the amount of information to be downloaded and the transmission time are likely to be restricted by the pre-set time slots. To transmit additional information that cannot be accommodated within a predetermined time slot, the information may be divided into different time slots of super frames and transmitted using each time slot assigned to the current group that appears in each super frame 14. The information may then be recombined at the reception side. However, in such case, additional processes are required for dividing and recombining the information. This is inconvenient for a mobile terminal, which is preferably configured to conserve energy consumption. Also, another problem is the fact that much time is required for all the information to be accumulated at the reception side.

Alternatively, instead of dividing and transmitting information in accordance with the format of the super frames, for example, weather forecast information that is originally intended to be transmitted using one time slot may be transmitted using two time slots (i.e., during the period from time t1 to time t3) so that the weather forecast information may be transmitted at once instead of having to be divided. However, in such case, the baseball information may not be transmitted at transmission time t2 as is originally intended (since the weather forecast information is being transmitted), and thereby, this information may not be transmitted until the next transmission time t2 of time slot 2 in the next super frame 14. Accordingly, when attempting to transmit more than the predetermined amount of information, the information downloading time for the current group or another group may be increased, and thereby, the efficient downloading may not always be realized.

It is also noted that information to be transmitted does not always require one time slot's worth of communication resources. However, even in the case of downloading information that does not reach the capacity of one time slot, since a pre-set fixed signal format is used, information resources are allotted in time slot units. Thus, efficient downloading may not always be obtained in regard to communication resource usage efficiency, for example.

SUMMARY OF THE INVENTION

Accordingly, it is an object of the present invention to improve downloading efficiency of transmission data.

The present invention, according to one aspect, provides an information downloading apparatus that downloads differing sets of information to predetermined groups to which a mobile terminal may belong, the apparatus including:

a buffer configured to receive sets of transmission data addressed to the groups;

a scheduler configured to select from a plurality of information channels an information channel for transmitting a set of transmission data of the sets of transmission data received at the buffer, the selection being made so that the sets of transmission data with differing destination addresses are transmitted using differing information channels; and a transmission unit for transmitting the set of transmission data using the selected information channel, the transmission unit being configured to transmit to each of the groups, through a control channel, information pertaining to whether a set of transmission data exists, the information channel to be used if the set of transmission data exists, and a data length of the set of transmission data, the control channel including a plurality of time slots that are associated with the groups.

The present invention, according to another aspect, provides an information downloading apparatus that downloads differing sets of information to predetermined groups to which a mobile terminal belongs, the apparatus including:

a buffer configured to receive sets of transmission data addressed to the groups;

a scheduler configured to determine a transmission timing for transmitting the sets of transmission data to the groups according to data length information of the sets of transmission data stored in the buffer; and a transmission unit for transmitting the sets of transmission data through an information channel according to conditions set by the scheduler, the transmission unit being configured to transmit to each of the groups, through a control channel, information pertaining to whether a set of transmission data exists, a transmission timing for the set of transmission data if the set of transmission data exists, and a data length of the set of transmission data, the control channel including a plurality of time slots that are associated with the groups.

The present invention, according to another aspect, provides, an information downloading apparatus, including:

a control channel having a plurality of time slots; and an information channel for downloading download information that is assigned to the time slots of the control channel;

wherein the time slots of the control channel include identification information for specifying the information channel that is to be used to download a set of download information.

In one embodiment of the present invention, the set of download information to be downloaded by the information channel may be transmitted after a predetermined offset time period elapses with respect to a corresponding time slot of the control channel.

According to another embodiment of the present invention, the identification information of the control channel may include information pertaining to a channel number and a data length.

The present invention, according to another aspect, provides an information downloading apparatus including:

a control channel having a plurality of time slots; and an information channel for downloading download information that is assigned to the time slots of the control channel;

wherein the time slots of the control channel include identification information for specifying a download timing for downloading a set of download information.

According to one embodiment of the present invention, the identification information may include information pertaining to an offset time period with respect to a corresponding time slot of the control channel, the offset information being used to prevent overlapping of differing sets of download information.

The present invention, according to another aspect, provides an information downloading apparatus that downloads differing sets of information to predetermined groups to which a mobile terminal belongs, the apparatus including:

a channel selecting unit (scheduler) configured to select from a plurality of information channels an information channel for transmitting a set of transmission data, the selection being made so that sets of transmission data with differing destination addresses are transmitted through differing information channels; and a transmission unit for transmitting the set of transmission data using the selected information channel, the transmission unit being configured to transmit to each of the groups, through a control channel, information pertaining to whether a set of transmission data exists, an information channel to be used if the set of transmission data exists, and a data length of the set of transmission data, the control channel including a plurality of time slots that are associated with the groups.

The present invention, according to another aspect, provides an information downloading apparatus that downloads differing sets of information to predetermined groups to which a mobile terminal belongs, the apparatus including:

a transmission timing determination unit (scheduler) configured to determine a transmission timing for transmitting sets of transmission data addressed to the groups according to data length information of the sets of transmission data;

a transmission unit for transmitting the sets of transmission data through an information channel according to conditions set by the transmission timing determination unit, the transmission unit being configured to transmit to each of the groups, through a control channel, information pertaining to whether a set of transmission data exists, a transmission timing of the set of transmission data if the transmission data exists, and a data length of the set of transmission data, the control channel including a plurality of time slots that are associated with the groups.

BRIEF DESCRIPTION OF THE DRAWINGS

FIG. 1 is a diagram illustrating a prior art example of information downloading using multicast technology;

FIG. 2 is a table illustrating an exemplary correspondence between a time slot number and a multicast group;

DESCRIPTION OF THE PREFERRED EMBODIMENTS

In the following, preferred embodiments of the present invention are described with reference to the accompanying drawings. It is noted that, for the sake of convenience, the preferred embodiments of information downloading apparatuses illustrated below are described as being implemented in a base station apparatus that establishes wireless communication with a mobile terminal. However, the information downloading apparatus of the present invention is not limited to such an arrangement and may be implemented in a base station control apparatus that controls the base station, or some other superordinate apparatus of the base station, for example. Alternatively, at least a portion of the functions of the information downloading apparatus of the present invention may be implemented in the base station and/or a superordinate apparatus of the base station.

First Embodiment

Figure 3:
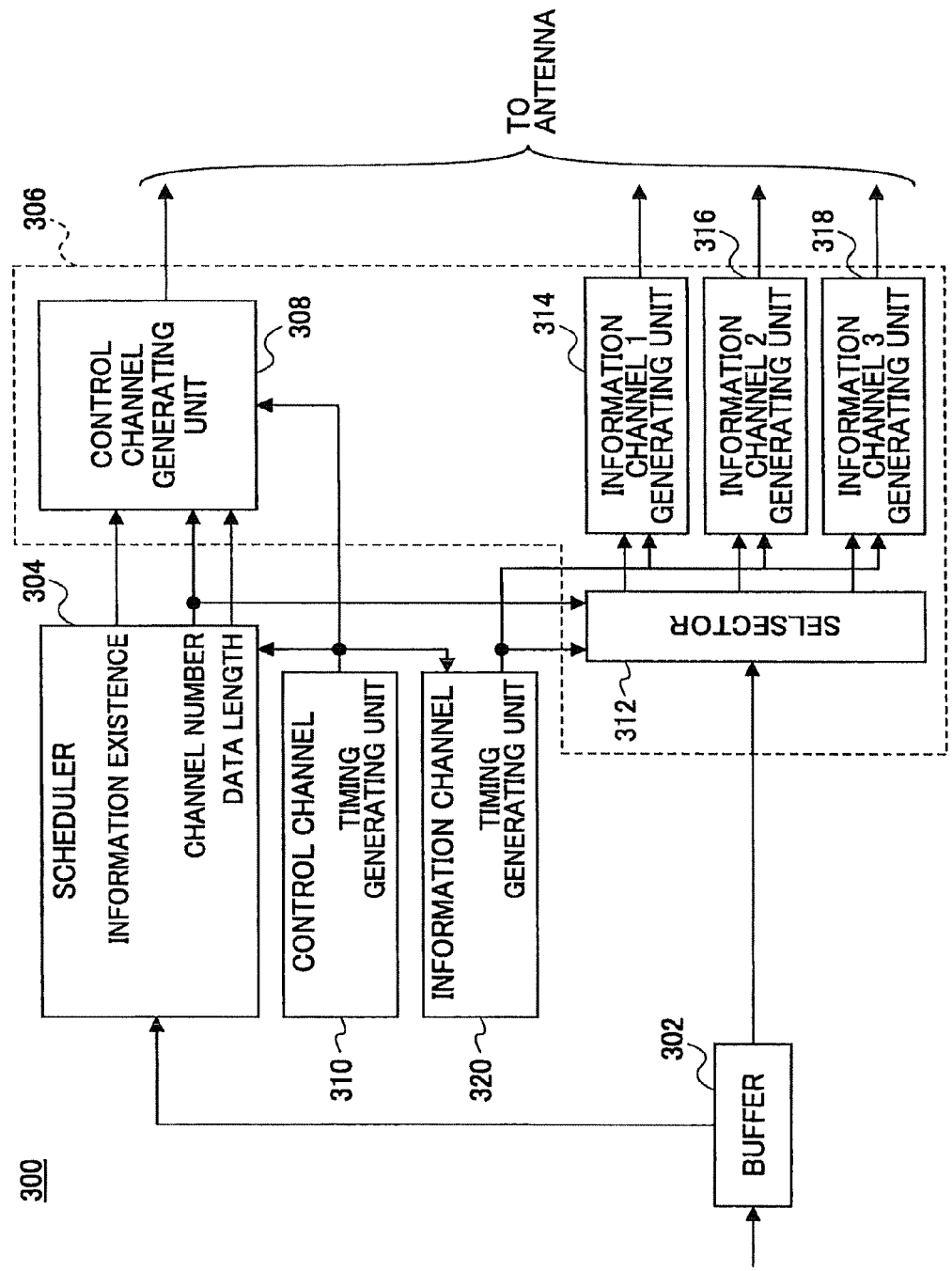
FIG. 3 is a block diagram showing a configuration of an information downloading apparatus according to a first embodiment of the present invention.

FIG. 3 is a block diagram showing an information downloading apparatus 300 according to a first embodiment of the present invention. In this example, information transmitted from a network (not shown) through a suitable interface (not shown) is stored in a buffer 302. The buffer 302 is coupled to a scheduler 304. The scheduler 304 is coupled to a control channel generating unit 308 that forms a part of a transmission unit 306. At the control channel generating unit 308, a control channel is generated using time slots that are associated with different multicast groups. In this way, control data may be transmitted to each group. Also, a control channel timing generating unit 310 provides information pertaining to the time slots and the transmission timing to the scheduler 304 and the control channel generating unit 308.

The buffer 302 may be coupled to an information channel 1 generating unit 314, an information channel 2 generating unit 316, or an information channel 3 generating unit 318 via a selector 312. The information channels correspond to communication resources that may be allotted using frequencies and spread codes, for example. In the present embodiment, predetermined channel numbers are used to identify the information channels; however, it is noted that the present invention is not limited to the use of channel numbers and any identification information that is capable of identifying an information channel may be used. The selector 312 uses a channel number from the scheduler 304 as well as timing information from the information channel timing generating unit 320 to conduct a selection operation. As is illustrated, the control channel generating unit 308, the selector 312, the information channel generating units 314, 316, and 318 for the information channels 1, 2, and 3, respectively, are comprehensively included in the transmission unit 306. That is, the output of the transmission unit 306 includes the output from the control channel generating unit 308, and the respective outputs from the information channel generating units 314, 316, and 318 for the information channels 1, 2, and 3. These outputs are output from an antenna (not shown) as a control channel and information channels, respectively.

In the following, the operation of the information downloading apparatus 300 is described. The buffer 302 receives transmission data that are transmitted as download information, and provides information pertaining to the amount of transmission data (buffer amount) for each multicast group to the scheduler 304. In turn, the scheduler 304 first determines whether download information exists for each group (information existence), and reports the determination result to the control channel generating unit 308. If it is determined that there is no download information for a given group, control data indicating the fact that no download data exist are generated at the control channel generating unit 308.

On the other hand, if it is determined that download information exists for a given group, the scheduler 304 selects from plural information channels one information channel that is suitable for downloading the corresponding information based on the data length of the transmission data. That is, after a predetermined period of time elapses from the end of the time slot (information channel) for the given group, an information channel that is capable of transmitting the download information is selected. In a case where there are plural information channels as candidates for conducting the transmission, the information channel with a smaller channel number may be selected in the present example. However, it is noted that this arrangement is not a prerequisite of the present invention and any of the any information channel suitable for the corresponding download information transmission may be used. Also, it is noted that in the present example, the predetermined period of time corresponds to a fixed offset time period that is set in the system beforehand. After the selection of the appropriate information channel, information pertaining to the selected information channel is conveyed to the control channel generating unit 308. In this way, information pertaining to the existence of transmission data, and in the case where the transmission data exist, the information channel to be used and the data length of the transmission data are transmitted to each group via a control channel.

The data length may correspond to an arbitrary value. The data length may be specified by the number of time slots as well as the number of bits, bytes, chips, and other forms of time units. In this way, large amounts of data may be consecutively downloaded. Also, precise resource allocation may be conducted with respect to small amounts of data that may not completely take up one slot.

Figure 4:
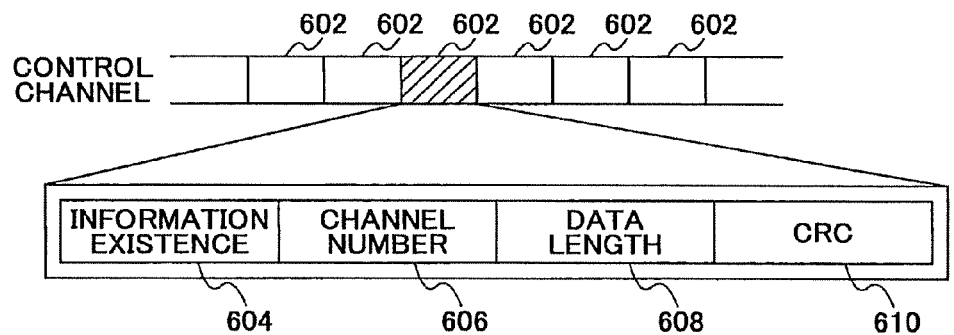
FIG. 4 is a diagram illustrating a control channel that is used in the first embodiment of the present invention.

FIG. 4 shows the contents of the control channel included in the output from the control channel generating unit 308. In the present example, each time slot 602 corresponds to each one of the plural multicast groups. In this way, information pertaining to the existence of transmission data (information existence) 604, the information channel to be used if the transmission data exist (channel number) 606, and the data length 608 of the transmission data are transmitted for each group. The control channel may also include CRC (Cyclic Redundancy Check) bits 610 for conducting error detection; however, the CRC is not a prerequisite of the present invention. It is noted that FIG. 4 is not a representation of a precise signal format of the control channel, and is rather a representation of the contents that may be included in the control channel. Accordingly, the order of the items within the control channel may be suitably adjusted, and also, other information items may be added as necessary or desired.

Referring back to FIG. 3, information pertaining to the selected information channel (channel number) is conveyed to the control channel generating unit 308, as well as the selector 312, and this information channel is used for transmission of the download information. In this way, download information from the buffer 302 is transmitted through the selector 312 to be output from the information channel generating units 314, 316, and 318 for the information channels 1, 2, and 3, based on the timing from the information channel timing generating unit 320. In the present embodiment, the information download apparatus 300 is implemented in a wireless base station, and thereby, the output information channels may be transmitted through wireless transmission along with the control channel. If the information downloading apparatus 300 is implemented as a superordinate apparatus of the base station, the outputs from the transmission unit 306 may be transmitted to the base station as control data and information data so that the data may in turn be transmitted from the base station as a control channel and information channels.

Figure 5:
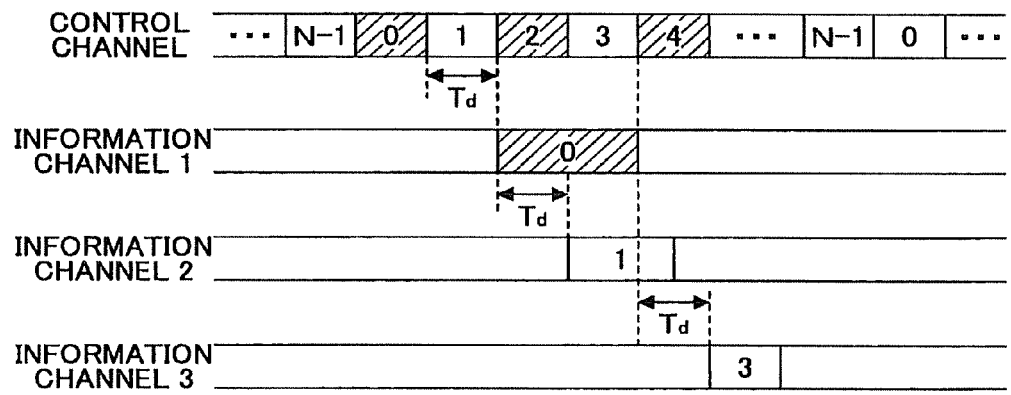
FIG. 5 is a diagram showing an exemplary set of a control channel and information channels that may be used in the first embodiment.

FIG. 5 is a diagram illustrating an exemplary set of a control channel and information channels that are output and transmitted from the transmission unit 306. As is shown, the control channel is made up of N time slots that may have values such as 256 or 1024, for example, and each time slot is associated with one of the multicast groups. The contents transmitted by the control channel may correspond to the output from the control channel generating unit 308 of FIG. 3. The N number of time slots may make up a super frame 402 as a whole, and control data pertaining to information downloading may be continually transmitted as a repetition of the super frames 402.

In the following description, it is assumed that the correspondence between a time slot and a multicast group as indicated in FIG. 2 is applied. According to the example of FIG. 5, in time slot 0 it is indicated that, download information pertaining to the news exists, and accordingly, after a predetermined offset time period Td elapses from the end of time slot 0, this download information is transmitted through information channel 1. This information corresponds to the output of the information channel 1 generating unit 314 of FIG. 3. Also, in time slot 1, it is indicated that download information pertaining to weather forecast exists, and accordingly, after a predetermined time period Td elapses from the end of time slot 1, this download information is transmitted through information channel 2. This information corresponds to the output of information channel 2 generating unit 316 of FIG. 3. In time slot 2, it is indicated that information pertaining to baseball does not exist, and thereby, no information is transmitted from the information channel. In time slot 3, it is indicated that download information pertaining to stocks exists, and accordingly, after a predetermined offset time period Td elapses from the end of time slot 3, this download information is transmitted through information channel 3. This information corresponds to the output of the information channel 3 generating unit 318.

In the above example, if the scheduler 304 is configured to select an information channel with a smaller channel number in a case where plural usable information channels exist, the information channel 1 may be used instead of the information channel 3 to transmit the stock information. Also, it is noted that although the predetermined offset time period Td is illustrated as being equivalent to the time period of one time slot in the present embodiment, such an arrangement is not a prerequisite of the present invention, and any suitable time period may be set as the offset time period.

Figure 6:
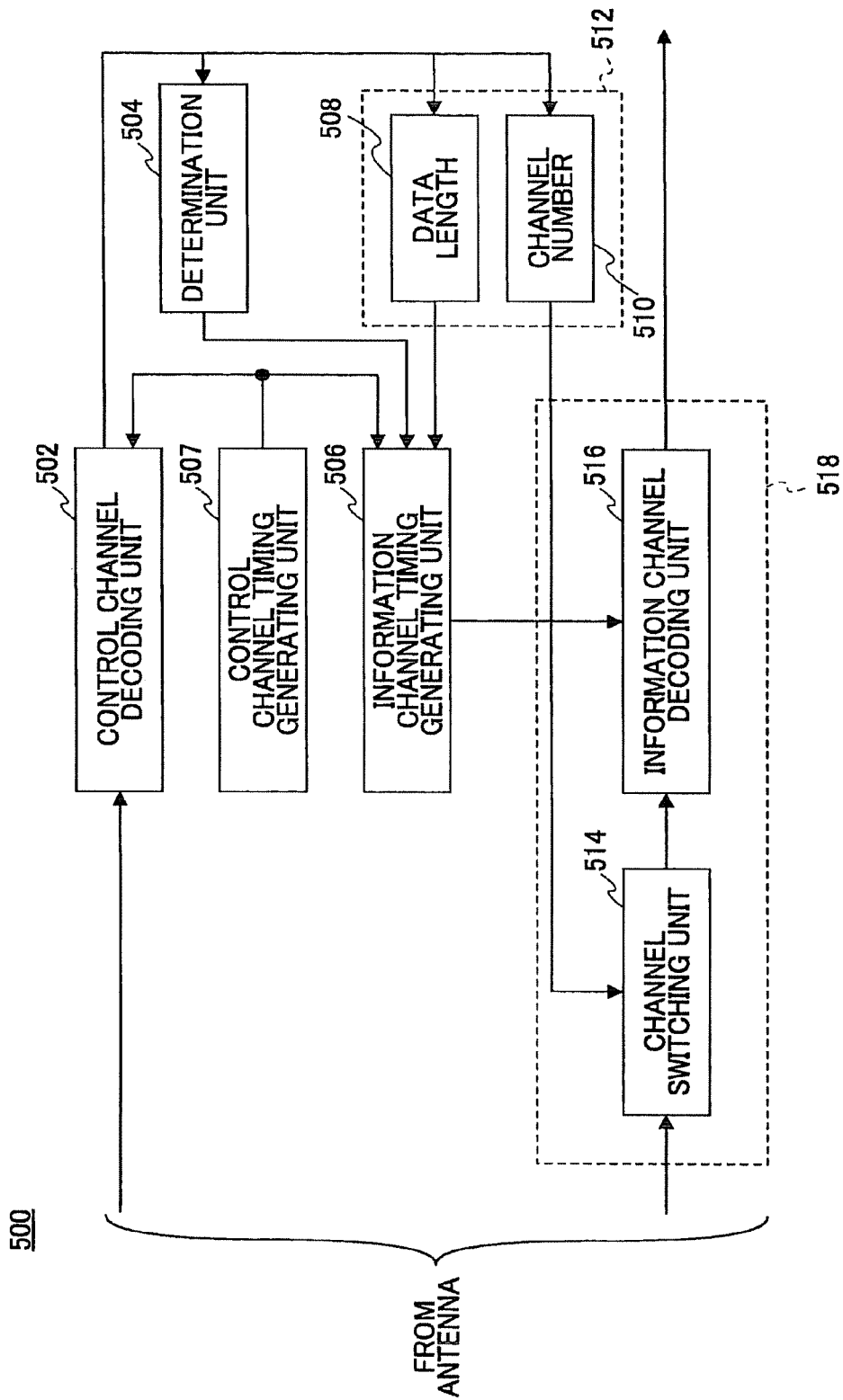
FIG. 6 is a block diagram showing a configuration of a portion of a mobile terminal that may be suitably used in the first embodiment.

FIG. 6 is a block diagram illustrating a configuration of a portion of a mobile terminal 500 that may be suitably used in the first embodiment of the present invention. The mobile terminal 500 includes a control channel decoding unit 502 for decoding control data included in a signal received via an antenna (not shown). The output of the control channel decoding unit 502 is coupled to a determination unit 504 that determines whether download information exists. The output of the determination unit 504 is coupled to an information channel timing generating unit 506 corresponding to management means for controlling the reception timing of information channels. The control channel decoding unit 502 and the information channel timing generating unit 506 are coupled to a control channel timing generating unit 507 for controlling the timing pertaining to the control channel. Also, the output of the control channel decoding unit 502 is coupled to a unit 508 for extracting the data length of the download information, and a unit 510 for extracting a channel number of the information channel to be used for transmitting the download information.

The units 508 and 510 are includes in an extraction unit 512, which is configured to extract control data other than data pertaining to the existence of download information. The output from the unit 510 concerned with the channel number is coupled to a switching unit 514 for switching to a channel designated by the unit 510 from among plural information channels. The output of the channel switching unit 514 is input to an information channel decoding unit 516 that is configured to output information data. The channel switching unit 514 and the information channel decoding unit 516 form a reception unit 518 for receiving the download information at the appropriate reception timing using the information channel designated by the control channel.

In the following, the operation of the mobile terminal 500 is described. The mobile terminal 500 receives control data for the multicast group to which it belongs through intermittent reception. Upon subscribing to a multicast group, the mobile terminal 500 acquires information pertaining to the time slot and the corresponding information thereof that it is to acquire. Using this information, the control channel timing generating unit 507 generates the reception timing for conducting the intermittent reception. A reception signal that is received from an antenna is demodulated by a demodulating circuit (not shown), and control data from a control channel are input to the control channel decoding unit 502, and decoded thereat. Then, the determination unit 504 determines whether download information exists. If it is determined that download information does not exist, this determination result is reported to the information channel generating unit 506, and the mobile terminal 500 waits for the arrival of the next set of control data. On the other hand, if it is determined that download information exists, the extraction unit 512 extracts additional information from the control data pertaining to the data length of the download information, and the information channel to be used for the information downloading (channel number). The information pertaining to the existence of the download information and the data length thereof are conveyed to the information channel generating unit 506. The information pertaining to the information channel to be used for the information downloading is conveyed from the extracting unit 512 to the channel switching unit 514 so that the channel may be set to the appropriate information channel. Then, the decoding unit 516 receives the download information based on the reception timing from the information channel generating unit 506, and decodes the received information to obtain information data.

For example, assuming that the mobile terminal 500 belongs to the group for news information, the mobile terminal 500 receives control data for time slot 0, decodes the data at the control channel decoding unit 502, and determines that download information exists at the determination unit 504. Thus, the extracting unit 512 extracts further information on the transmission data to determine that the data length of the transmission data is 20 ms, and the information channel 1 is to be used to conduct the information downloading. Then, the mobile terminal 500 receives the news information that is transmitted after the predetermined offset time period elapses from the end of the time slot 0 using the information channel 1.

According to the present embodiment, plural information channels are used to transmit download information. The information channel to be used for transmitting download information for a given group is conveyed to each group through a control channel. The manner in which the plural information channels are to be used may be suitably determined by the scheduler 304 within the information downloading apparatus 300 so that downloading efficiency may be improved.

It is noted that the embodiment described above is illustrated as having three information channels. However, the present invention is not limited to this arrangement, and any number of information channels that are defined by a frequency, a code, or a combination thereof, for example, may be used. Also, it is noted that although a common channel that may be shared by all users is conventionally used as the information channel, in some cases, a unique channel that is exclusively used by a single user may be used as well. That is, the information channel is concerned with appropriately transmitting download information, and thereby, the present invention may use a common channel or a unique channel, or use a unique channel when such channel is already established and use a common channel when a unique channel is not established. On the other hand, the control channel is concerned with controlling the intermittent operations of mobile terminals belonging to various groups, and thereby, a common channel shared by these mobile terminals and including time division time slots has to be used as the control channel.

Second Embodiment

Figure 7:
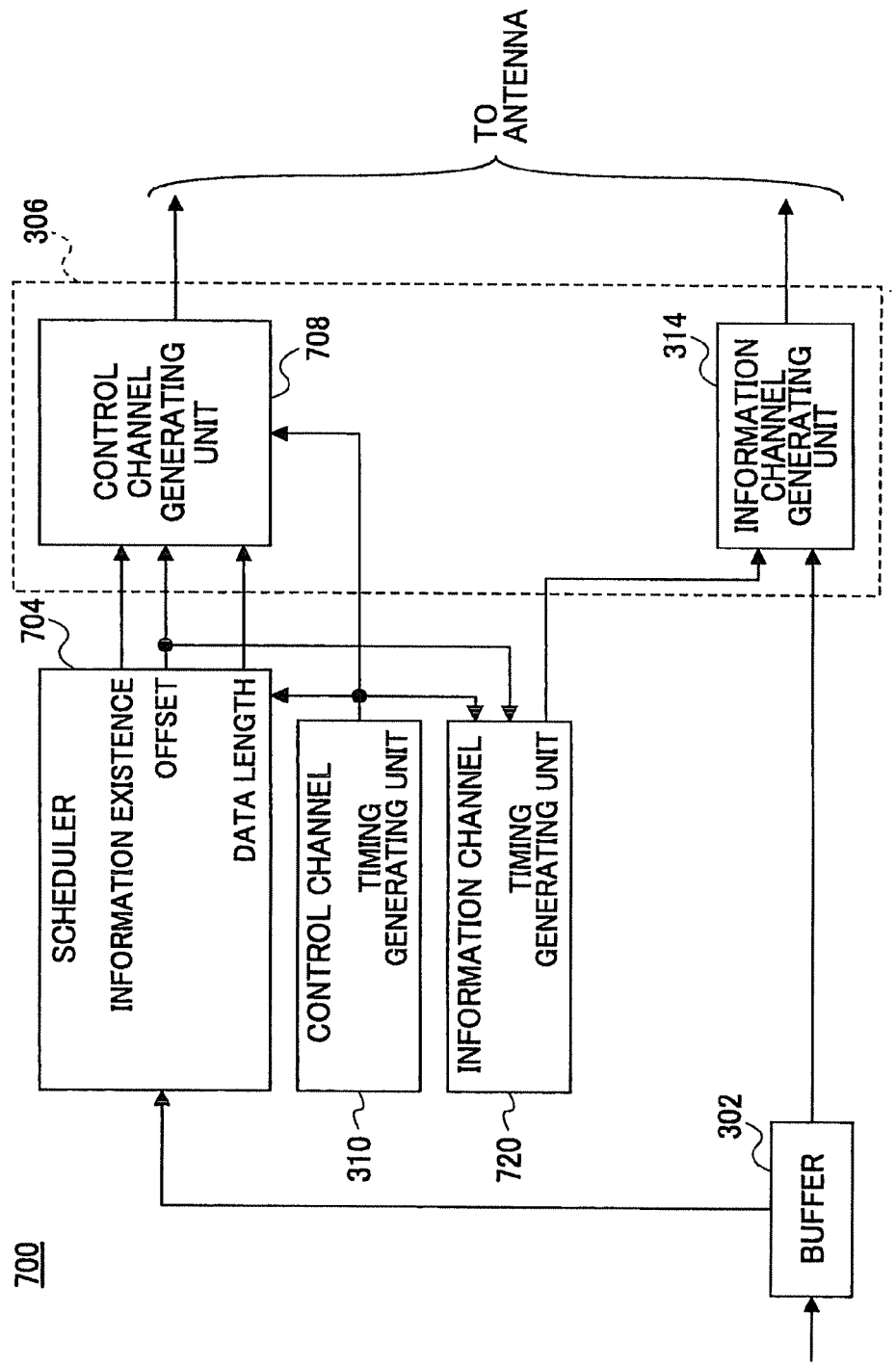
FIG. 7 is a block diagram showing a configuration of an information downloading apparatus according to a second embodiment of the present invention.

FIG. 7 is a block diagram illustrating a configuration of an information downloading apparatus 700 according to a second embodiment of the present invention. It is noted that elements of the present embodiment that are identical to those of the first embodiment are assigned the same numerical references and descriptions thereof are omitted. The information downloading apparatus 700 includes a buffer 302 and a scheduler 704 that is coupled to the buffer 302. The scheduler 704 determines, based on information pertaining to the amount of data from the buffer 302, whether download information exists and the data length thereof if such download information exists as in the first embodiment. The scheduler 704 differs from the first embodiment in that it conveys to a control channel generating unit 708 information pertaining to a time period that is to elapse from the end of a time slot after which download information may be transmitted (offset), such information being primarily based on the data length of the download information. In other words, according to the present embodiment, the offset is not set to a fixed value, and is rather a variable that may dynamically vary for each group. The offset information is also conveyed to an information channel timing generating unit 720, which in turn generates the transmission timing for the download information. Using this transmission timing, an information channel generating unit 314 transmits transmission data that are stored in the buffer 302.

Figure 8:
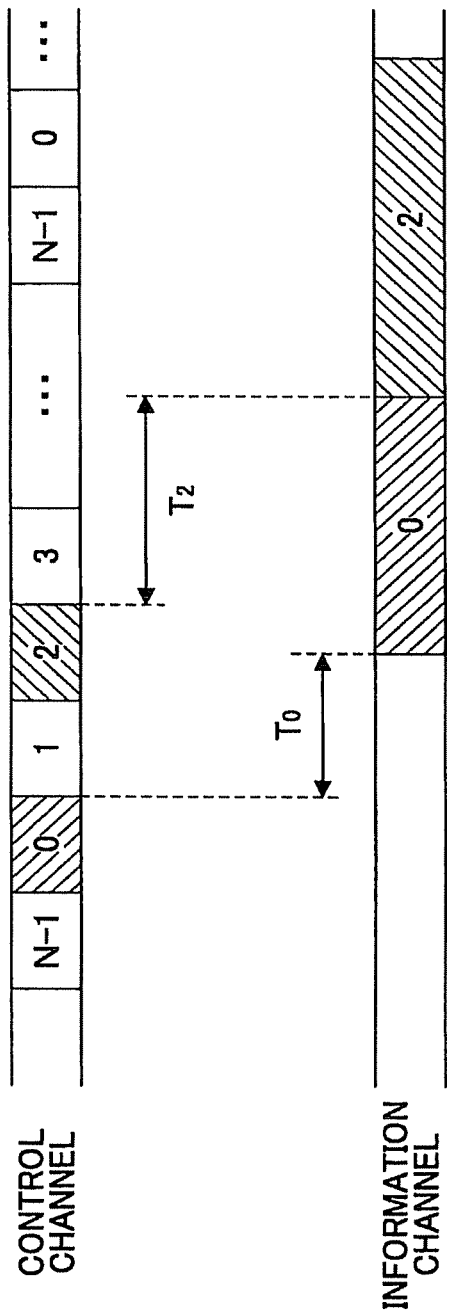
FIG. 8 is a diagram showing an exemplary set of a control channel and an information channel that may be used in the second embodiment.

FIG. 8 illustrates an exemplary set of a control channel and an information channel that may be output from the transmission unit 306 according to the present embodiment. In this example, the control channel includes N time slots numbered from 0 to N−1, and is configured to transmit sets of control data for the respective groups associated with the time slots. In the present embodiment, information pertaining to the existence of download data, the offset, and the data length are transmitted as the control data to each group. For example, in time slot 0, it may be indicated that download information pertaining to the news exists, and accordingly, this download information may be transmitted after the elapse of a certain time interval ($T_0$) from the end of the time slot 0. In time slot 1, it may be indicated that information pertaining to weather forecast does not exist. In time slot 2, it may be indicated that information pertaining to baseball exits, and accordingly, the download information may be transmitted after the elapse of a certain time interval ($T_2$) from the end of the time slot 2. It is noted that the values of the time intervals $T_0$ and $T_2$ are variable, and may depend mainly on the data length of the transmission data. In the present embodiment, the time interval may be set using an arbitrary time unit as with the data length, and thereby, the period of time during which the information channel is no used may be reduced so as to realize efficient information downloading.

Figure 9:
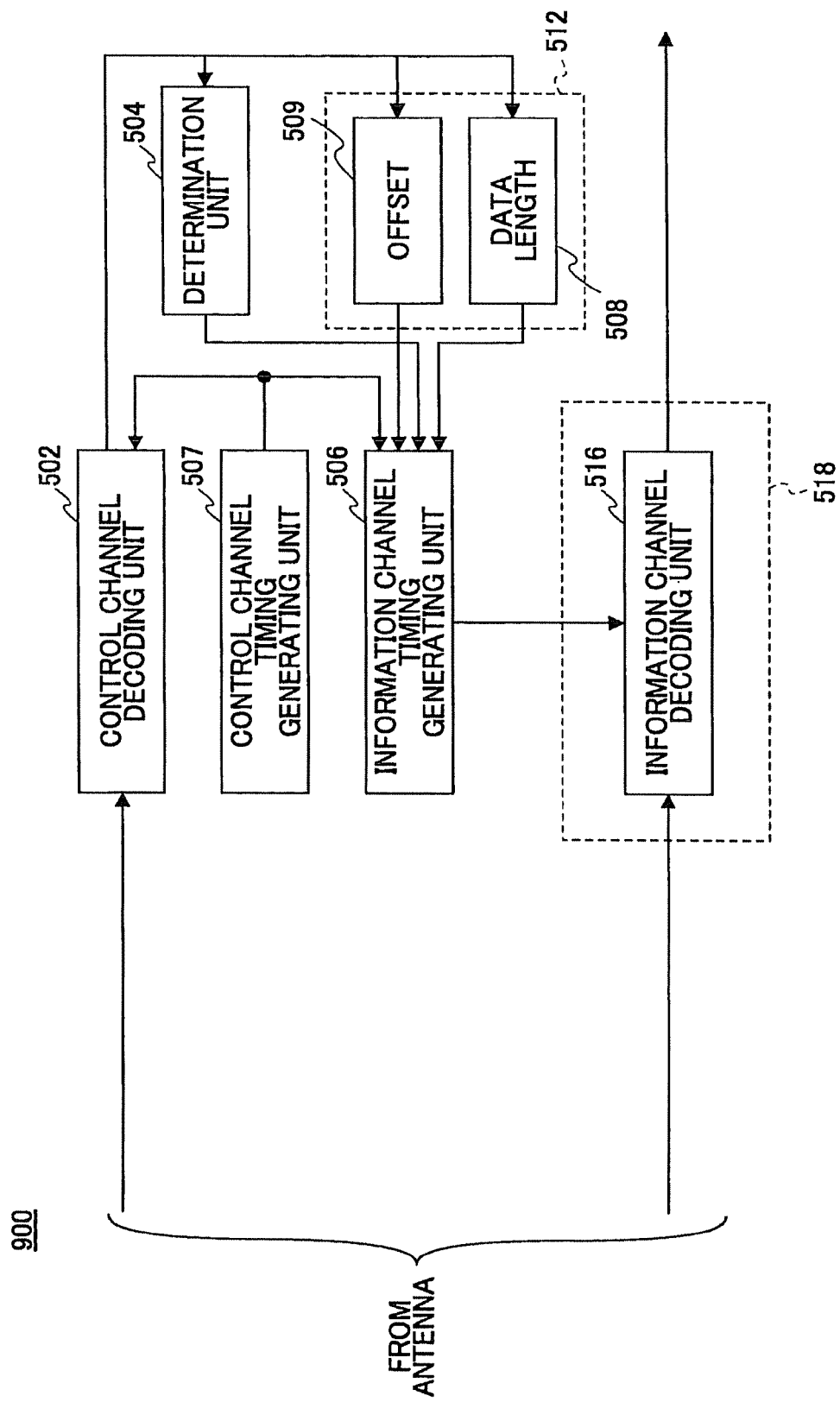
FIG. 9 is a block diagram showing a configuration of a portion of a mobile terminal that may be suitably used in the second embodiment.

FIG. 9 shows a configuration of a portion of a mobile terminal 900 that may be suitably used in the second embodiment of the present invention. It is noted that elements of the present embodiment that are identical to those shown in FIG. 6 are assigned the same numerical references and descriptions thereof are omitted. In the present example, a reception signal that is received from an antenna is demodulated through a demodulation circuit (not shown), and control data from the control channel are input to a control channel decoding unit 502. Then, at a determination unit 504, a determination is made as to whether download information exists, and the determination result is reported to an information channel timing generating unit 506. If it is determined that download information exists, information on the data length of the download information and the offset are further extracted from the control data at an extracting unit 512, and the extracted information is conveyed to the information channel timing generating unit 506. Then, an information channel decoding unit 516 receives the download information based on the reception timing from the information channel timing generating unit 506, and decodes the download information to obtain information data.

According to the present embodiment, the offset may be changed with respect to each group in transmitting download information. The length (duration) of the offset is reported to each group through the control channel. Also, the offset may be suitably determined by the scheduler 304 within the information downloading apparatus 300 so that information downloading efficiency may be improved.

Third Embodiment

A third embodiment of the present invention generally corresponds to a combination of the features of the first embodiment and the second embodiment of the present invention. Specifically, in the present embodiment, plural information channels are used, and the offset is arranged to be variable. It is noted that the elements of the present embodiment that are identical to those of the first and/or second embodiment are assigned the same numerical references and descriptions thereof are omitted.

Figure 10:
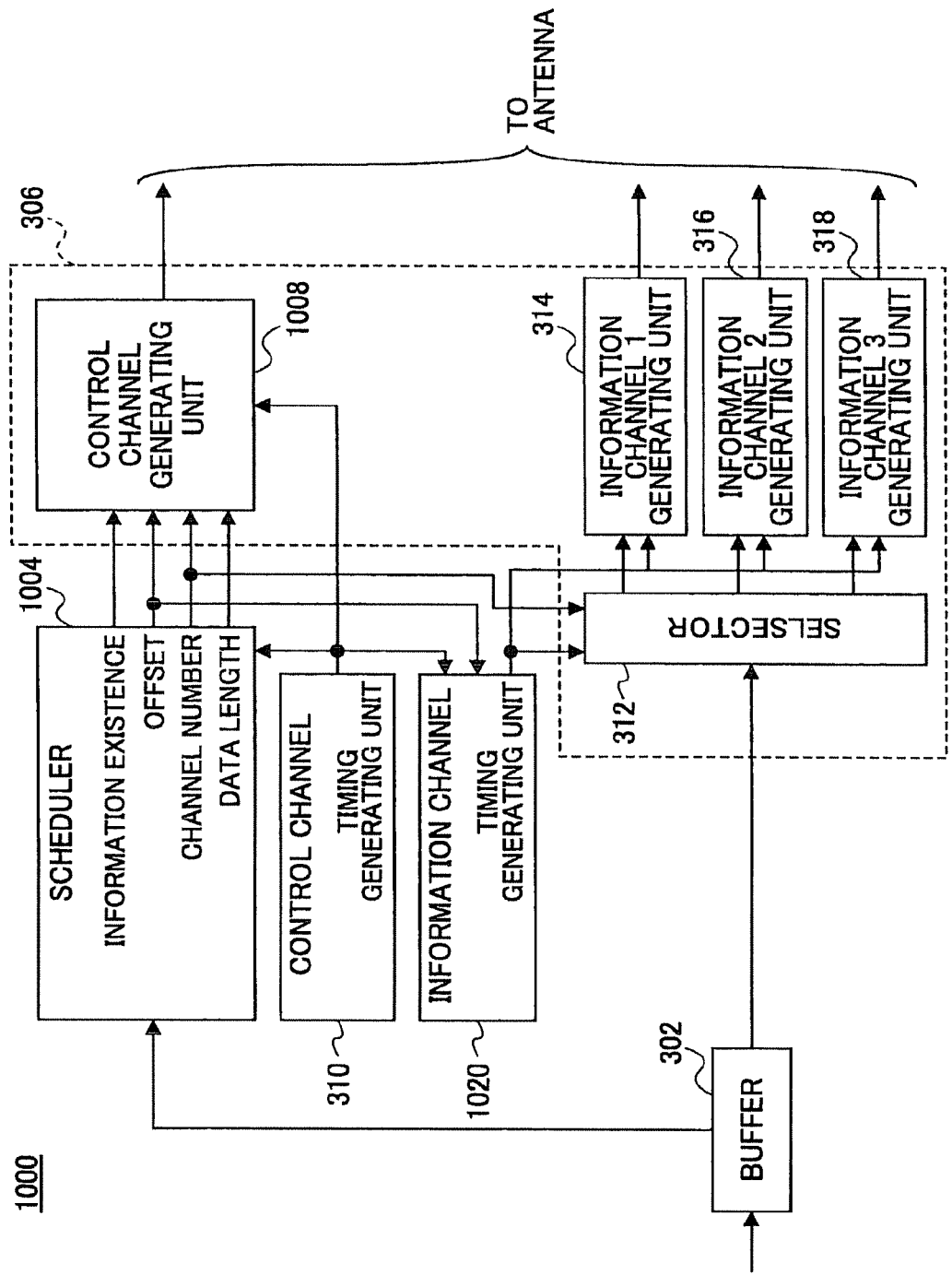
FIG. 10 is a block diagram showing a configuration of an information downloading apparatus according to a third embodiment of the present invention.

FIG. 10 is a block diagram showing a configuration of an information downloading apparatus 1000 according to the third embodiment. In the present embodiment, a scheduler 1004 determines the existence of download information, the offset, the channel number, and the data length, and reports the determination result to the control channel generating unit 1008. In the control channel generating unit 1008, a control channel that includes the above information is generated. Information pertaining to the offset is also supplied to the information channel timing generating unit 1020. The information pertaining to the channel number is also supplied to the selector 312.

Figure 11:
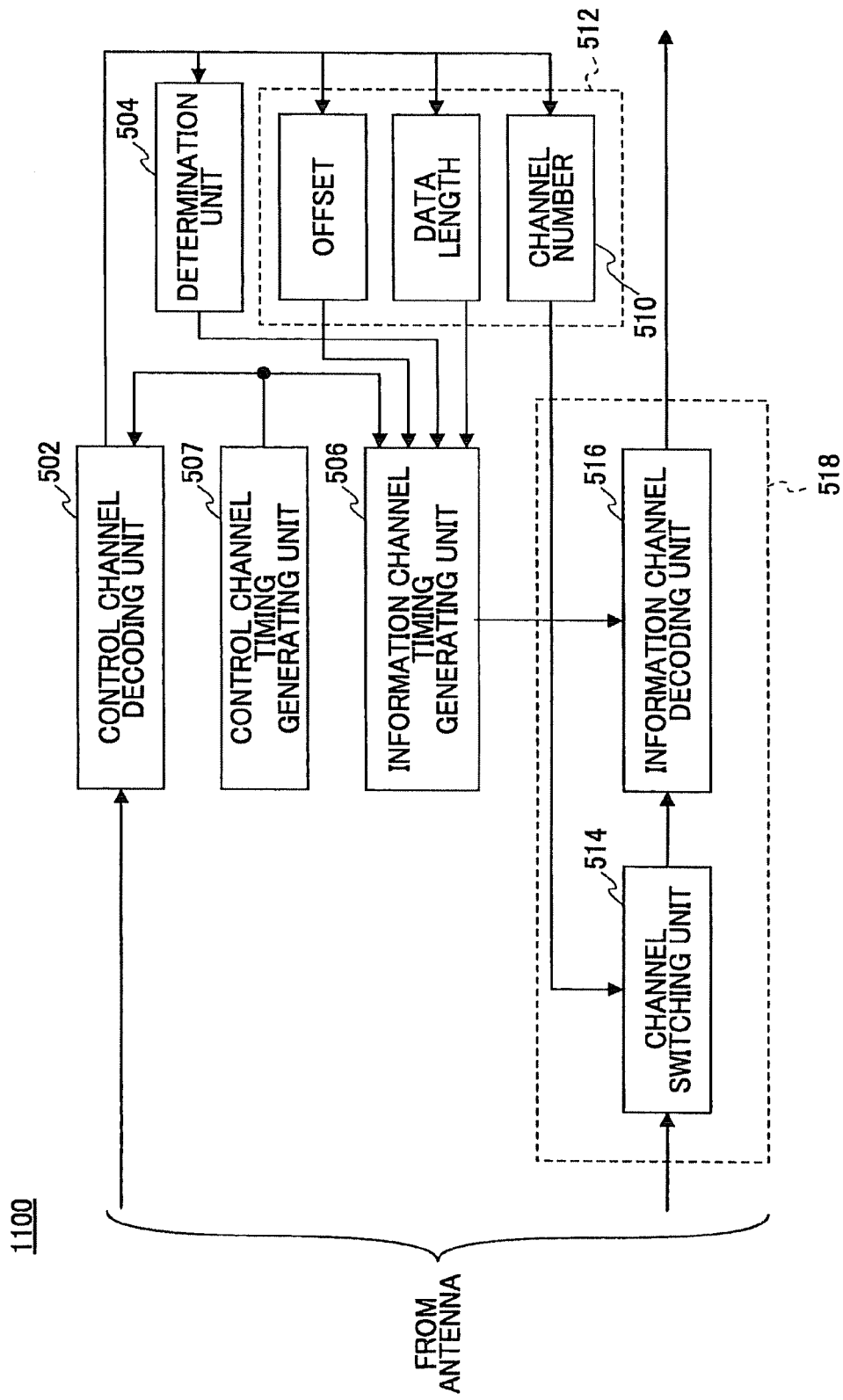
FIG. 11 is a block diagram showing a configuration of a portion of a mobile terminal that may be suitably used in the third embodiment.

FIG. 11 is a block diagram showing a configuration of a portion of a mobile terminal 1100 that may be suitably used in the third embodiment. In the present example, control data from the control channel are input to the control channel decoding unit 502 to be decoded thereat. Then, a determination unit 504 determines whether download information exists and reports the determination result to an information channel timing generating unit 506. If it is determined that download information exists, information pertaining to the data length of the download information, the offset, and the channel number are extracted at an extracting unit 512. The offset and the data length are also reported to the information channel timing generating unit 506. The channel number of the information channel to be used is reported to the channel switching unit 514 through the extracting unit 512 so that the channel is set to the appropriate information channel. Then, an information channel decoding unit 516 receives the download information based on the reception timing from the information channel timing generating unit 506, and decodes the download information to obtain information data.

According to the present embodiment, plural information channels are used, and the offset may differ depending on each group upon transmitting download information. In this way, efficient information downloading may be realized, and information may be quickly downloaded while improving the usage efficiency of communication resources for the information channels. It is noted that in the first example, information may be quickly downloaded to each group but the usage efficiency of each individual information channel is low. In the second embodiment, the information channel usage efficiency is very high but the information downloading timing is delayed compared to the first embodiment. According to the present embodiment, a time directional offset and a frequency (or spread code) may be dynamically assigned according to the amount of transmission data that are stored in the buffer. Since the channel number of the information channel and the offset may be suitably adjusted in the present embodiment, the scheduler 1004 may be configured to select a suitable channel number and a suitable offset value for each downloading operation.

Fourth Embodiment

Figure 12:
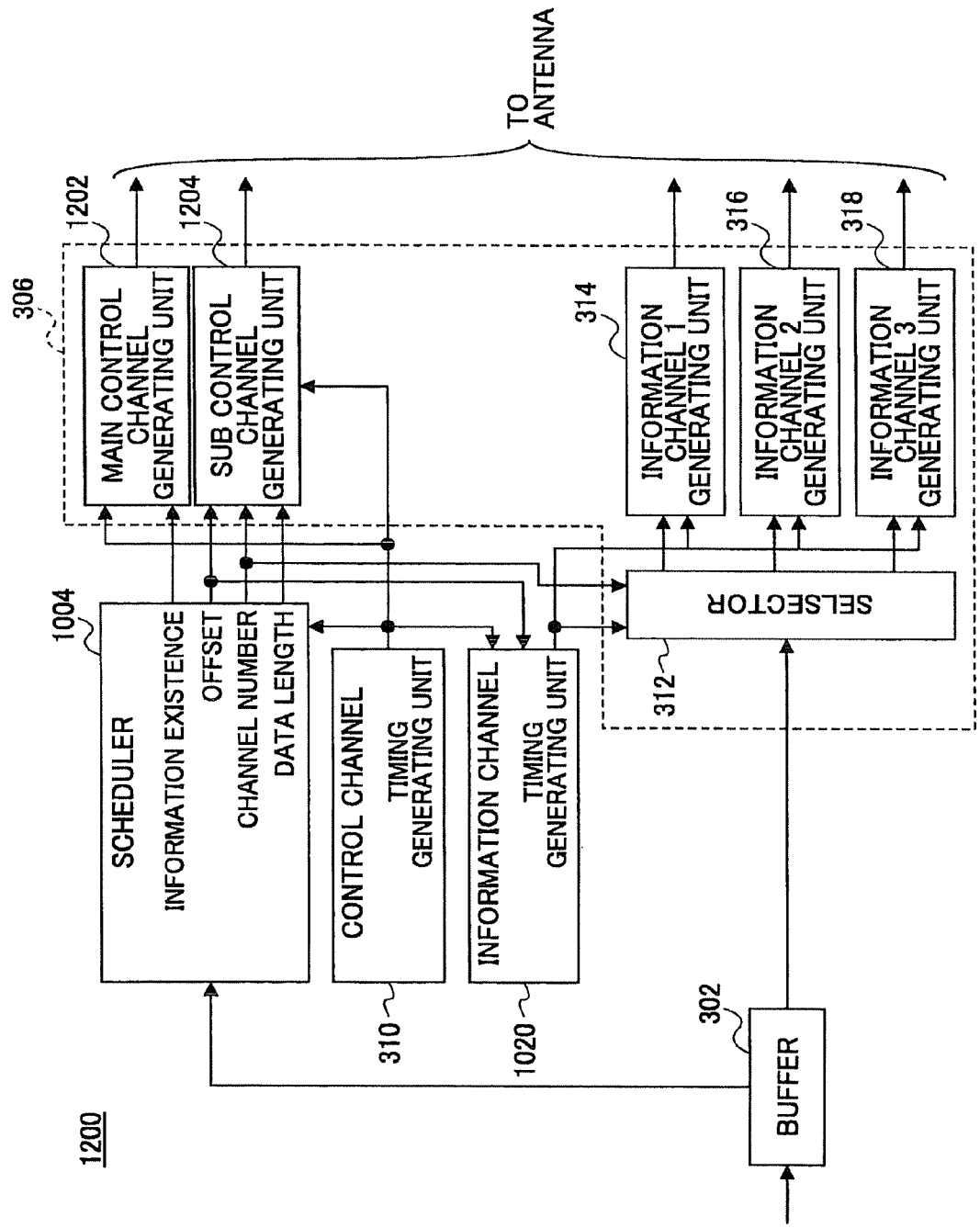
FIG. 12 is a block diagram showing a configuration of an information downloading apparatus according to a fourth embodiment of the present invention.

FIG. 12 is a block diagram showing a configuration of an information downloading apparatus 1200 according to a fourth embodiment of the present invention. It is noted that elements of the present embodiment that are identical to those of the first through third embodiment are assigned the same numerical references and description thereof are omitted. In the present embodiment, a scheduler 1004 determines the existence of download information, the offset, the channel number, and the data length based on information from a buffer 302. Of the determination results, information on the existence of download information is reported to a main control channel generating unit 1202, and information pertaining to the data length, the offset, and the channel number are reported to a sun control channel generating unit 1204. As is described, in the present embodiment, a main control channel generating unit 1202 for transmitting information indicating the existence (or non-existence) of download information, and a sub control channel generating unit 1204 for transmitting other control data (e.g., data length, offset, and channel number) are used. The main control channel and the sub control channel are each made up of time slots that are allotted to the respective groups. The offset (deviation) between these control channels are maintained at zero or a fixed value.

Figure 13:
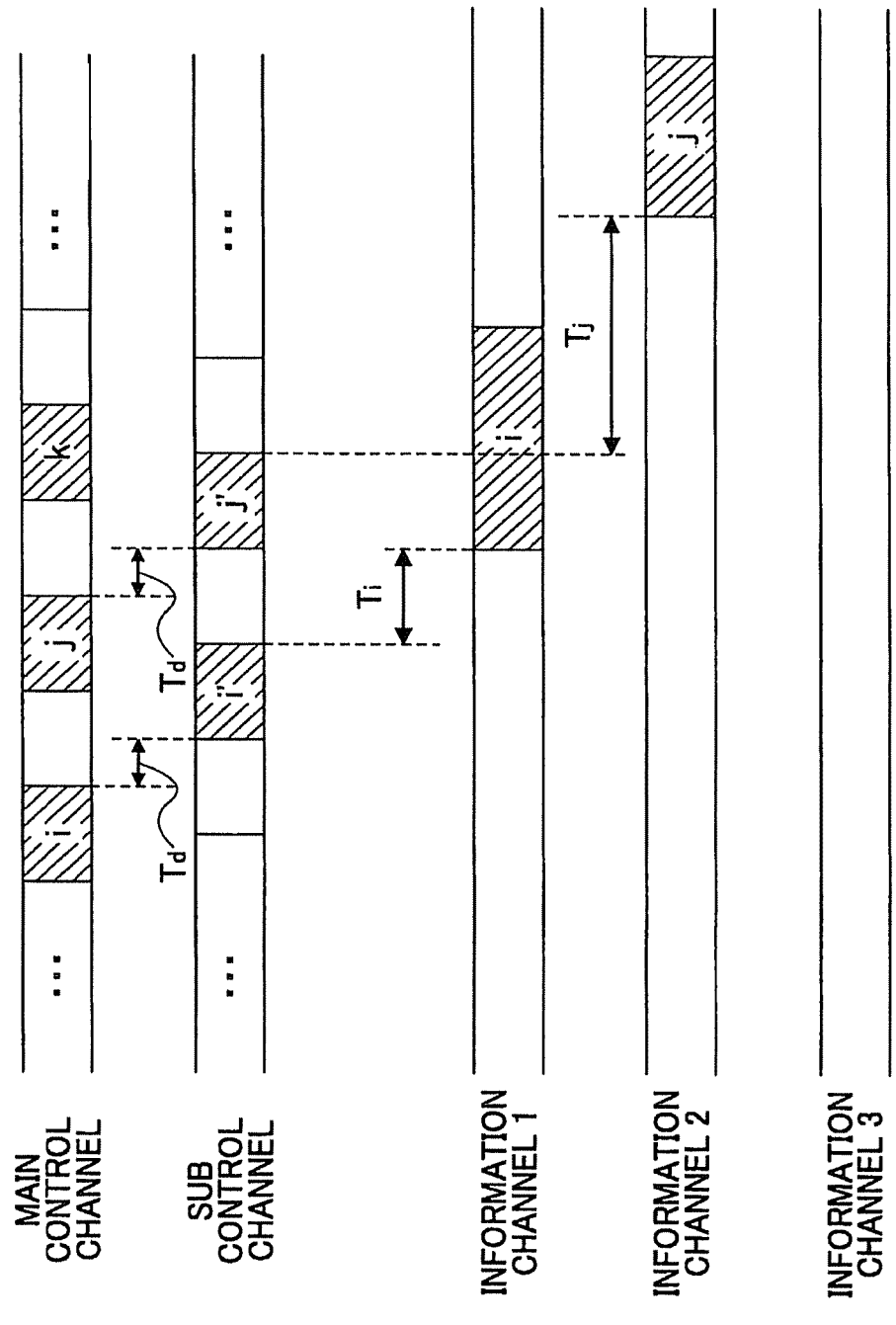
FIG. 13 is a diagram showing an exemplary set of a main control channel, a sub control channel, and information channels that may be used in the fourth embodiment.
Figure 14:
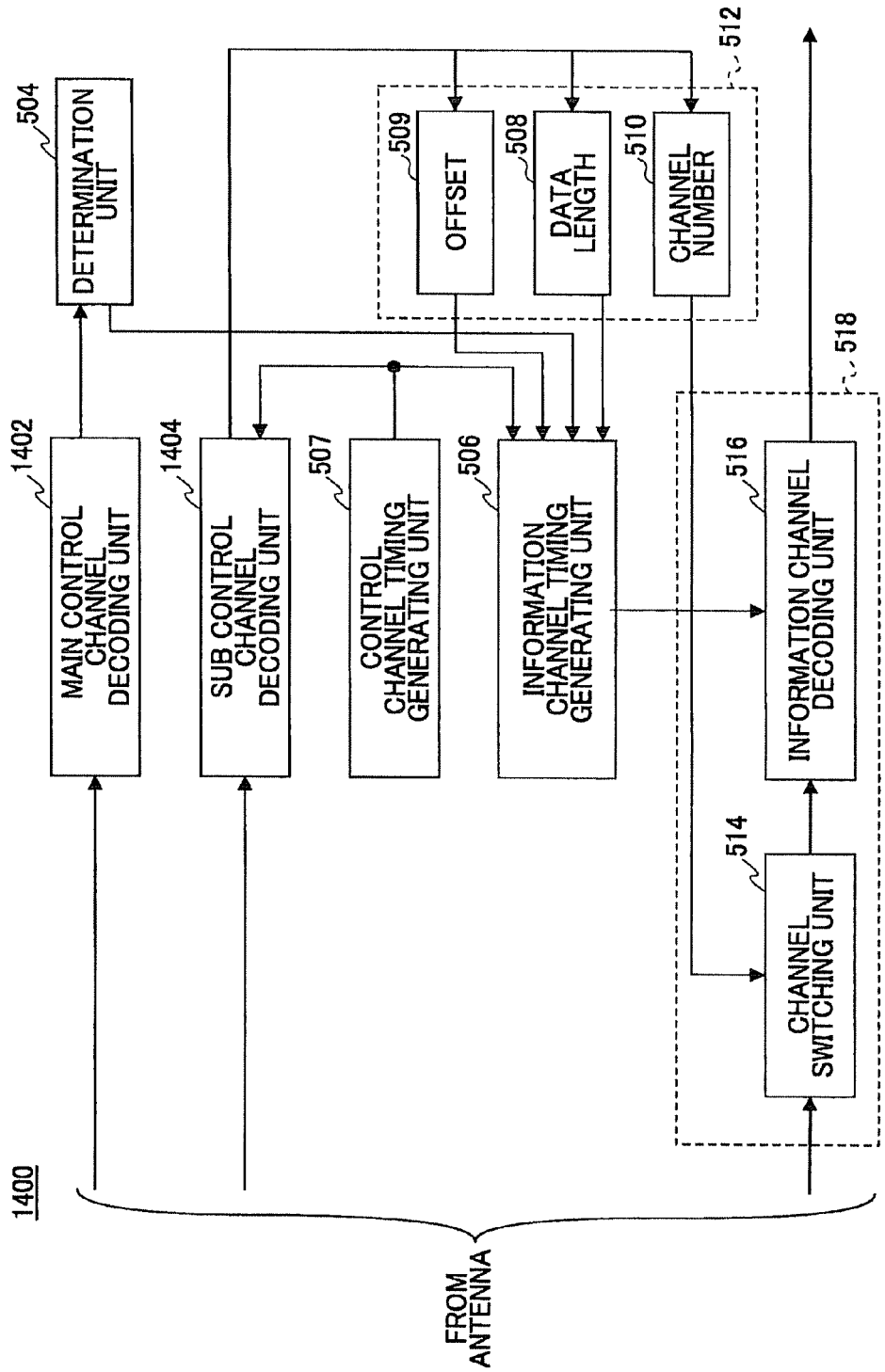
FIG. 14 is a block diagram showing a configuration of a portion of a mobile terminal that may be suitably used in the fourth embodiment.

FIG. 13 shows an exemplary set of a main control channel, a sub control channel, and information channels 1, 2, and 3 that may be output in the present embodiment. According to the present example, in time slot (i) of the main control channel, it is indicated that download information exists, and in a corresponding time slot (i') of the sub control channel, the data length, the offset, and the channel number are indicated. Accordingly, after the elapse of offset time Ti from the end of the time slot (i'), the download information may be transmitted using information channel 1, for example. Similarly, in another time slot (j) of the main control channel, it is indicated that download information exists, and in a corresponding time slot (j') of the sub control channel, the data length, the offset, and the channel number are indicated. Accordingly, after the elapse of offset time Tj from the end of the time slot (j'), the download information may be transmitted using information channel 2, for example. In another time slot (k) of the main control channel, it is indicated that download information does not exist, and in this case there is not information that is to be transmitted at the sub control channel. In the present embodiment, the temporal difference between the main control channel and the sub control channel is maintained at a predetermined offset values Td; however, the offsets Ti and Tj indicating the offset for starting the transmission of download information correspond to variables that may be suitably adjusted FIG. 14 is a block diagram showing a configuration of a portion of a mobile terminal 1400 that may be suitably used in the fourth embodiment. In the present example, the control channel is divided into two channels, namely, the control channel and the sub control channel upon being transmitted. Accordingly, the mobile terminal 1400 of the present embodiment includes a main control channel decoding unit 1402 and a sub control channel decoding unit 1404. The main control channel decoding unit 1402 decodes the information included in the main control channel and conveys the decoded information to a determination unit 504. The determination unit 504 determines whether download information exists and reports the determination result to an information channel timing generating unit 506. Other control data are supplied to the extracting unit 512 through the sub control channel decoding unit 1404 wherein the data length, the offset, and the channel number are extracted at units 508, 509, and 510, respectively. The data length and the channel number are then supplied to a channel switching unit 514, and accordingly, data in the information channel may be received through an information channel decoding unit 516.

According to the present embodiment, features and advantages that are similar to those of the third embodiment are realized, and additionally, the control channel is divided into a main control channel and a sub control channel. For example, a conventional paging indicator channel (PICH) may be used as the main control channel for transmitting information pertaining to the existence of the transmission data, and an associated S-CCP channel may be used as the sub control channel for transmitting other information. Accordingly, in the present embodiment, conventional technology may be applied to achieve desired effects of the present invention with relative ease.

Fifth Embodiment

Figure 15:
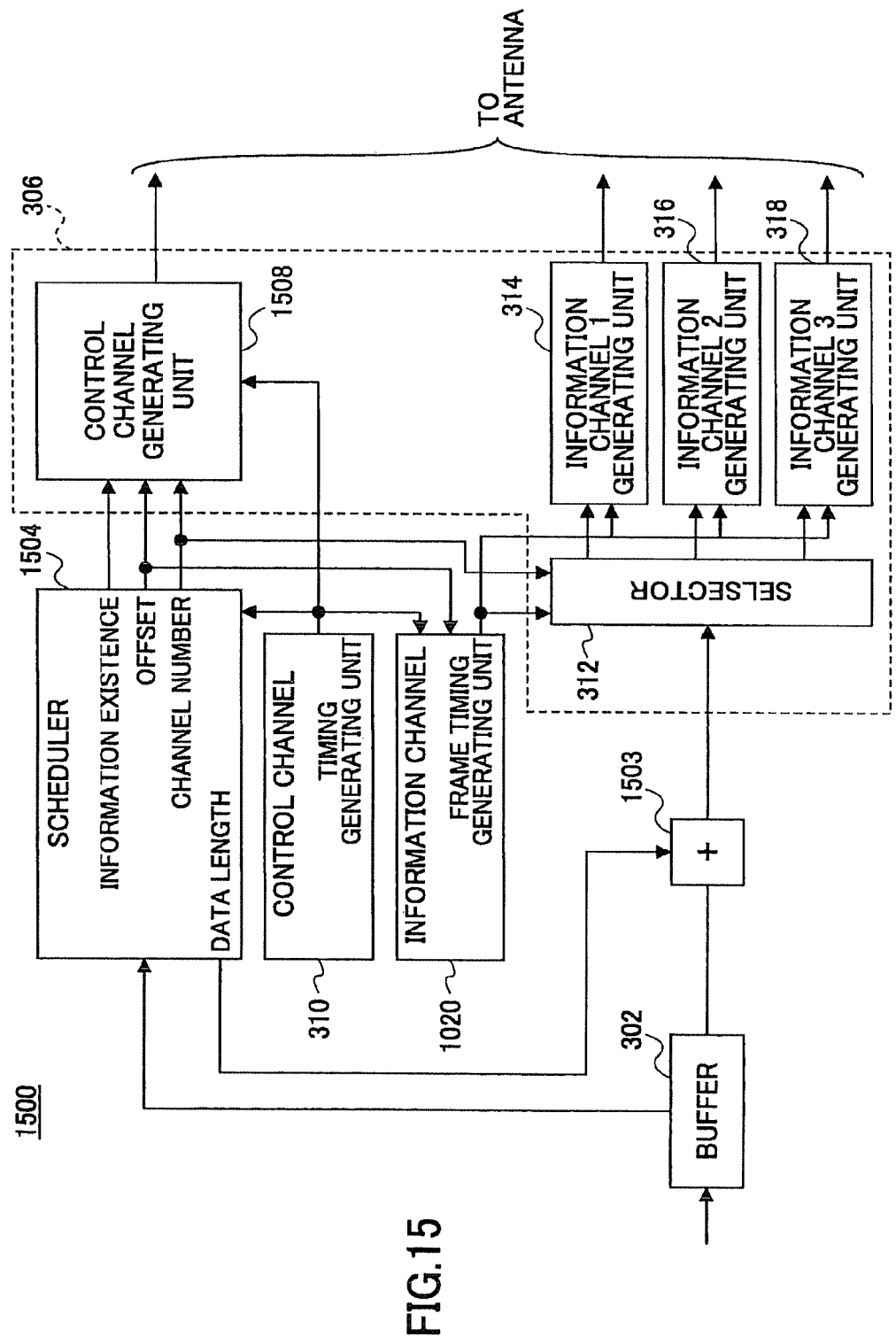
FIG. 15 is a block diagram showing a configuration of an information downloading apparatus according to a fifth embodiment of the present invention.

FIG. 15 is a block diagram showing a configuration of an information downloading apparatus according to a fifth embodiment of the present invention. The present embodiment is generally identical to the third embodiment except for the manner in which the data length of the download information is handled. In the first through fourth embodiments, information pertaining to the data length is transmitted through the control channel; however, in the present embodiment, information on the data length is transmitted through the information channel. Specifically, the data length information is inserted in the information channel to be used as header information.

In the present embodiment, a scheduler 1504 determines whether download information exists, the offset, the channel number, and the data length of the download information as in the previously described embodiments. Then, information on the data length is supplied to an input on one side of an adder 1503. The input on the other side of the adder 1503 is coupled to an output of a buffer 302. This adder 1503 may attach the information pertaining to the data length as header information for the download information. The download information having the information pertaining to the data length attached thereto is conveyed to a suitable information channel generating unit through a selector 312, and is transmitted therefrom.

Figure 16:
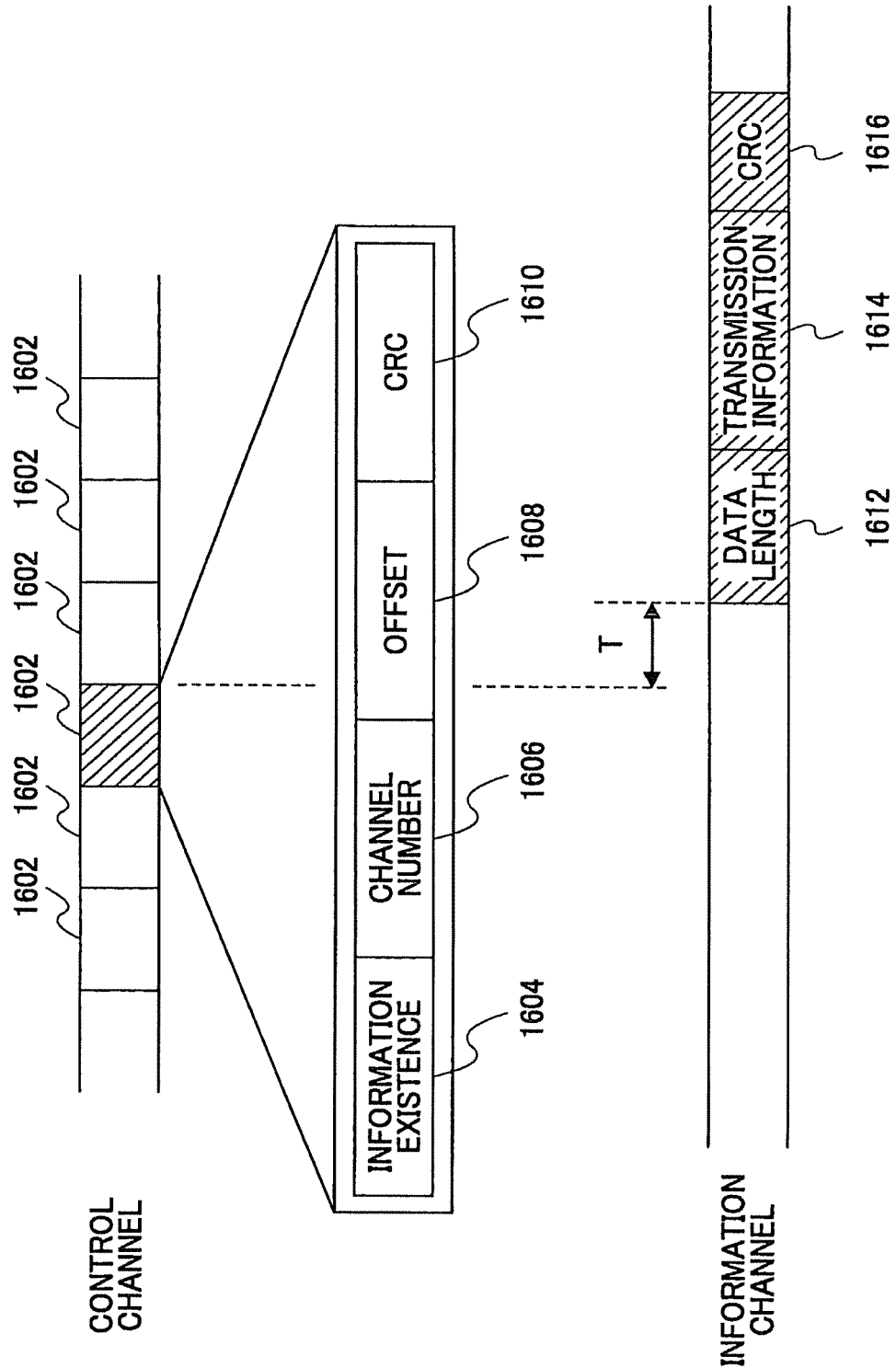
FIG. 16 is a diagram showing an exemplary set of a control channel and an information channel that may be used in the fifth embodiment.

FIG. 16 is a diagram showing an exemplary set of a control channel and an information channel that may be used in the fifth embodiment of the present invention. According to this example, each time slot 1602 is allotted to one of plural multicast groups, and for each group information pertaining to the existence of transmission data (information existence) 1604, the information channel to be used if transmission data exist (channel number) 1606, the offset 1608 are transmitted. After the end of a given time slot and after a designated offset time T provided by the offset 1608 elapses, the transmission of the download information may start. In the information channel being illustrated, the data length of the download information 1612, the download information 1614, and a CRC 1616 are transmitted. It is noted that the CRC is not a prerequisite of the present invention and may therefore be omitted as necessary or desired.

Figure 17:
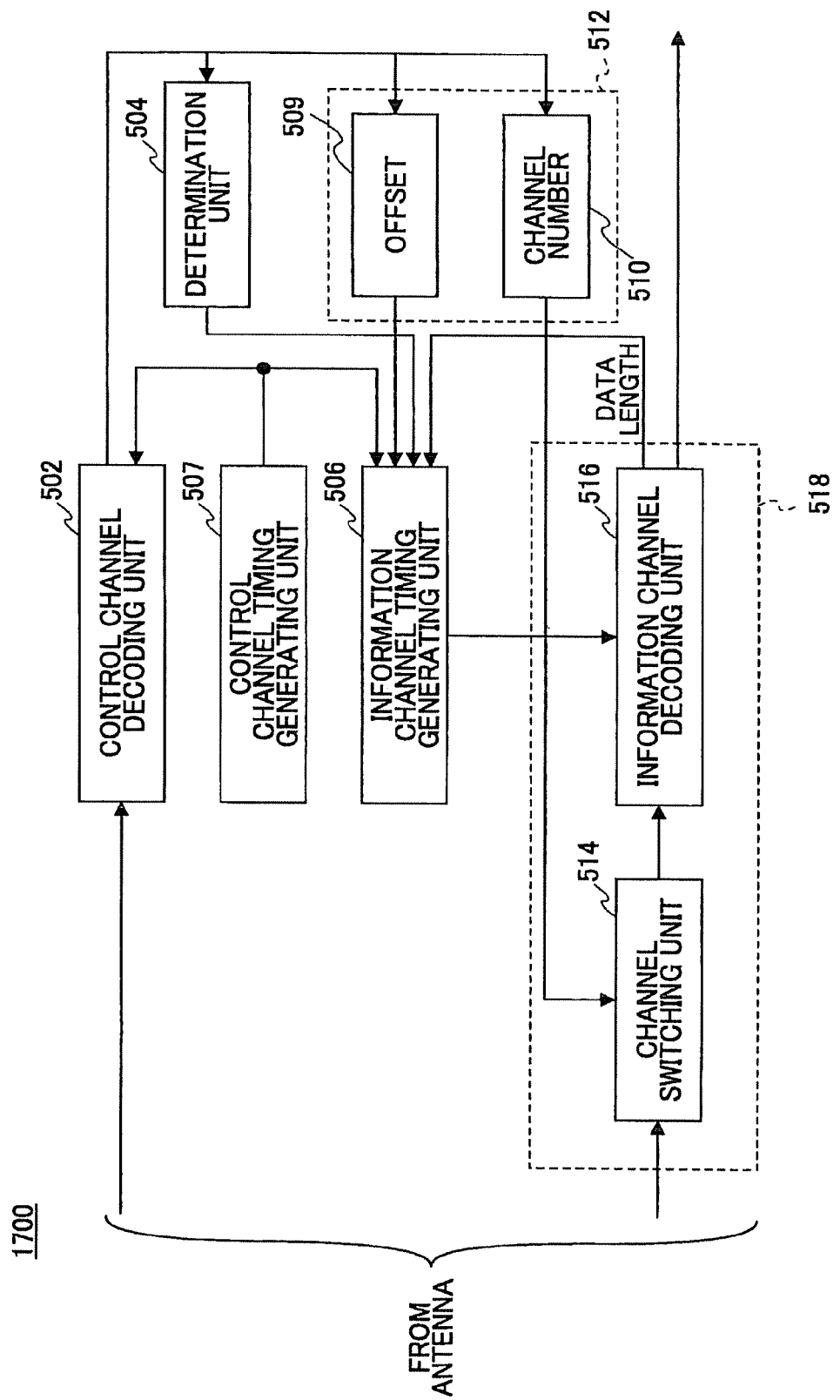
FIG. 17 is a block diagram illustrating a configuration of a portion of a mobile terminal that may be suitably used in the fifth embodiment.

FIG. 17 is a block diagram showing a configuration of a portion of a mobile terminal 1700 that may be suitably used in the fifth embodiment of the present invention. The mobile terminal 1700 of the present example is generally identical to the mobile terminal 1100 of FIG. 3, except for the manner in which it handles information on the data length of download information. According to the present embodiment, the data length is transmitted as header information in an information channel, and thereby, information on the data length is extracted at an information channel decoding unit 516, and is supplied to an information channel timing generating unit 506. The present embodiment may be advantageous in that the amount of information contents to be transmitted by the control channel may be reduced.

Sixth Embodiment

Figure 18:
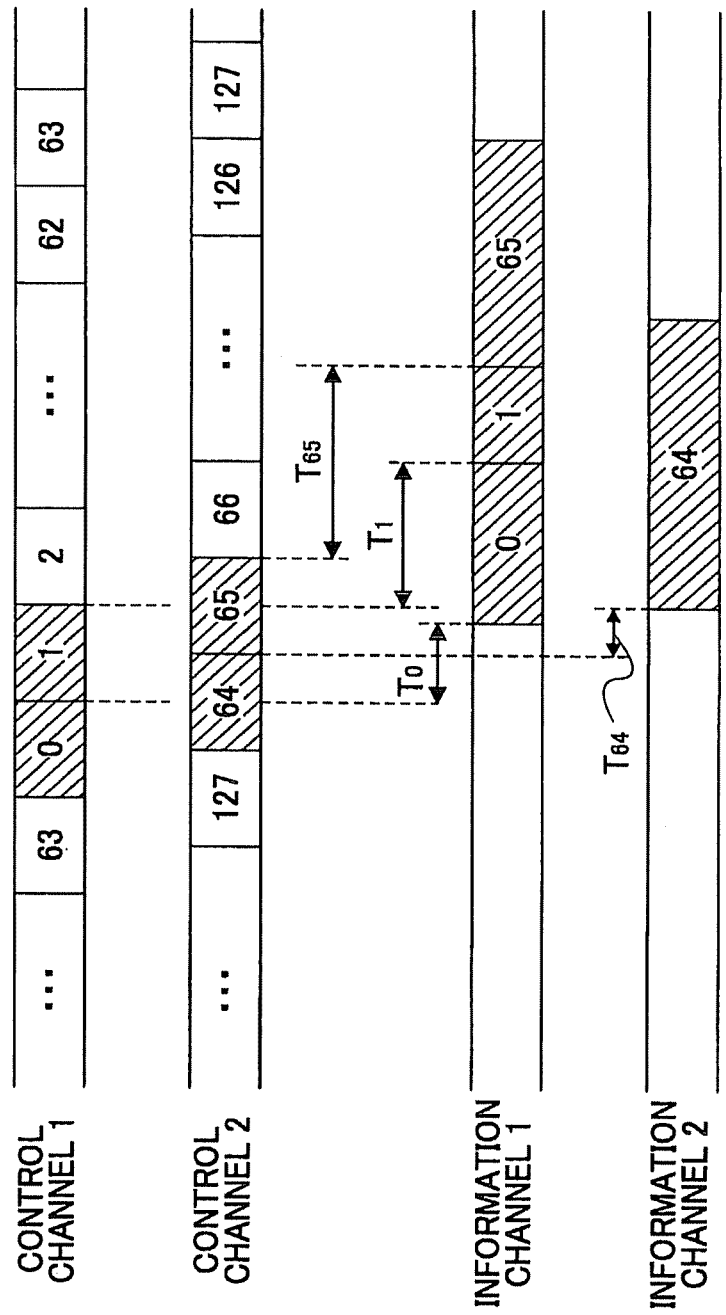
FIG. 18 is a diagram showing an exemplary set of control channels and information channels that may be used in a sixth embodiment of the present invention.

FIG. 18 is a diagram illustrating an exemplary set of control channels and information channels according to a sixth embodiment of the present invention. According to the present embodiment, a first control channel and a second control channel are provided to conduct parallel transmission of control data to two groups. In the example illustrated in the drawing, transmission of control data with respect to the groups corresponding to time slots 0 through 63 may be conducted by the first control channel, and transmission of control data with respect to the groups corresponding to the time slots 64 through 127 may be conducted by the second control channel. For example, three sets of download information that are offset by offsets $T_0$, $T_1$, and $T_{65}$ from time slots 0, 1, and 65, respectively, may be transmitted by information channel 1, and download information offset by $T_{64}$ from time slot 64 may be transmitted by information channel 2.

According to the present embodiment, the control channel generating unit of the transmission unit uses plural time slots that may temporally overlap to transmit information on the existence of download information, the information channel to be used if the download information exists, the transmission timing of transmission data, and the data length of the transmission data to plural groups. By providing plural control channels as in the present embodiment, the control data for plural groups may be transmitted in a parallel manner. The present embodiment may be particularly advantageous for systems in which a relatively large number of groups exist.

According to an embodiment of the present invention, the scheduler may be configured to select an information channel from plural information channels and determine to conduct transmission of transmission data with the selected information channel so that transmission data with differing destinations may be transmitted through differing information channels. The transmission unit may be configured to transmit to each group, information pertaining to the existence of transmission data, the information channel to be used if the transmission data exist, and the data length of the transmission data through the control channel. The control channel includes plural time slots that are each associated with one of plural groups. Download information for the respective groups may be quickly downloaded through plural information channels so that the data downloading efficiency may be improved.

Also, according to another embodiment of the present invention, the scheduler may be configured to determine the transmission timing for transmitting the transmission data for each group based on the data length of the transmission data that is stored in the buffer. The transmission unit may be configured to transmit for each group, information pertaining to the existence of transmission data, the transmission timing if the transmission data exist, and the data length of the transmission data through the control channel. The transmission timing (start time and end time) may be determined according to a given data length, and thereby, data downloading efficiency may be improved.

An information downloading apparatus according to an embodiment of the present invention may be implemented in a base station that conducts wireless communication with a mobile terminal, or alternatively, the information downloading apparatus may be implemented in a superordinate apparatus that controls the base station, for example. The information downloading apparatus may be made up of one single apparatus, or plural apparatuses. For example, the scheduler (304, 704, 1004, 1504) and the transmission unit (306) may be provided in separate apparatuses. In other words, the information downloading apparatus of the present invention may be realized in any form so long as its characteristic features may ultimately be realized.

It is noted that preferred embodiments of the present invention have been described above; however, the present invention is not limited to these embodiments, and variations and modifications may be made without departing from the scope of the present invention.

What is claimed is:

1. A wireless communication method, comprising:
 transmitting, by a transmitter, frequency information for transmitting data to a multicast group and offset information indicating an offset amount of a timing at which the data is to be transmitted with respect to a predetermined periodic reference timing;
 transmitting, by the transmitter, the data to the multicast group using a frequency determined by the frequency information at a transmission timing determined by the offset information;
 receiving, by a receiver, the frequency information and the offset information transmitted by the transmitter; and
 receiving, by the receiver, data being transmitted to the multicast group based on the frequency information and the offset information,
 wherein a time interval between the predetermined periodic reference timing and the transmission timing of the data is set to differing time lengths depending on the offset amount indicated by the offset information; and
 the frequency information and the offset information are transmitted prior to transmission of the data when data transmission is to be performed.

* * * * *